United States Patent
Olian, Jr. et al.

(10) Patent No.: US 11,918,735 B2
(45) Date of Patent: Mar. 5, 2024

(54) DUAL METERED INHALER

(71) Applicant: Pure Scientific Technologies, Inc., Las Vegas, NV (US)

(72) Inventors: Irwin A. Olian, Jr., Las Vegas, NV (US); L. Michael Cutrer, Huntington Beach, CA (US); Philip Cacayorin, McMinnville, OR (US)

(*) Notice: Subject to any disclaimer, the term of this patent is extended or adjusted under 35 U.S.C. 154(b) by 548 days.

(21) Appl. No.: 16/882,326

(22) Filed: May 22, 2020

(65) Prior Publication Data

US 2020/0368459 A1 Nov. 26, 2020

Related U.S. Application Data

(60) Provisional application No. 63/019,119, filed on May 1, 2020, provisional application No. 62/966,389, filed on Jan. 27, 2020, provisional application No. 62/852,806, filed on May 24, 2019.

(51) Int. Cl.
*A61M 15/00* (2006.01)

(52) U.S. Cl.
CPC .... *A61M 15/0066* (2014.02); *A61M 15/0003* (2014.02); *A61M 15/0021* (2014.02); *A61M 15/0091* (2013.01); *A61M 2202/0208* (2013.01); *A61M 2202/025* (2013.01); *A61M 2202/04* (2013.01); *A61M 2202/06* (2013.01); *A61M 2205/3584* (2013.01); *A61M 2206/16* (2013.01)

(58) Field of Classification Search
CPC ............ A61M 15/0003; A61M 15/002; A61M 15/0066; A61M 15/0095; A61M 15/0096; A61M 11/00–08; A61M 15/00–085
See application file for complete search history.

(56) References Cited

U.S. PATENT DOCUMENTS

| | | | | |
|---|---|---|---|---|
| 5,033,463 | A | * | 7/1991 | Cocozza ........... A61M 15/0065 128/203.23 |
| 6,125,844 | A | * | 10/2000 | Samiotes .......... A61M 15/0091 128/200.23 |
| 7,461,649 | B2 | | 12/2008 | Gamard |
| 8,327,845 | B2 | | 12/2012 | Weinstein |
| 9,675,768 | B2 | | 6/2017 | Fink |
| 10,332,631 | B2 | | 6/2019 | Miller |
| 2002/0148462 | A1 | | 10/2002 | Fugelsang |
| 2003/0079744 | A1 | * | 5/2003 | Bonney ............. A61M 15/0043 128/203.12 |

(Continued)

FOREIGN PATENT DOCUMENTS

EP 3102056 12/2016

OTHER PUBLICATIONS

Hess, Dean R.; et al. "The History and Physics of Heliox," Respiratory Care, Jun. 2006 vol. 51 No. 6. 5 pages.

(Continued)

*Primary Examiner* — Valerie L Woodward
(74) *Attorney, Agent, or Firm* — Fish IP Law, LLP

(57) ABSTRACT

An inhaler having first and second user-operable controllers configured to independently meter first and second amounts of a physiologically active substance and a pressurized gas, respectively, to a user is disclosed. A regulator is configured to release a dose to the mouthpiece in some embodiments. Triggering can be activated by one or more of (1) the user drawing a breath through the mouthpiece, and (2) the user operating a trigger.

20 Claims, 3 Drawing Sheets

(56) References Cited

U.S. PATENT DOCUMENTS

| | | | | |
|---|---|---|---|---|
| 2003/0200964 | A1* | 10/2003 | Blakley | A61M 15/025 128/200.23 |
| 2005/0123483 | A1* | 6/2005 | Gamard | A61M 15/009 128/200.23 |
| 2007/0062525 | A1 | 3/2007 | Bonney | |
| 2008/0173301 | A1* | 7/2008 | Deaton | A61M 15/009 128/203.12 |
| 2010/0210565 | A1 | 8/2010 | Rasor et al. | |
| 2014/0251321 | A1* | 9/2014 | Benson | A61M 15/009 128/200.23 |
| 2015/0034077 | A1 | 2/2015 | Kraft | |
| 2016/0045685 | A1* | 2/2016 | Hyde | A61M 15/008 128/200.14 |
| 2018/0308572 | A1 | 10/2018 | Manice | |
| 2019/0175850 | A1* | 6/2019 | Petit | A61M 15/009 |

OTHER PUBLICATIONS

Ujváry, Istvan; et al. "Human Metabolites of Cannabidiol: A Review on Their Formation, Biological Activity, and Relevance in Therapy," Cannabis Cannabinoid Res. 2016; 1(1): 90-101. 21 pages.
Particle Size Analyzers, https://www.micromeritics.com/Product-Showcase/Particle-Size-Instruments-Group.aspx. 5 pages.
Intro to Vaporization—Learn About Vaporizing Cannabis, https://www.medicaljane.com/category/cannabis-classroom/consuming-cannabis/vaporization/#heating-sources. 4 pages.
Chevrolet, Jean-Claude. "Helium oxygen mixtures in the intensive care unit," Crit Care. 2001; 5(4): 179-181. 5 pages.
"What is the Blockchain Communication Protocol?", https://www.quora.com/What-is-the-Blockchain-Communication-Protocol. 2 pages.
"Spin Of Subatomic Particles," https://www.encyclopedia.com/science/encyclopedias-almanacs-transcripts-and-maps/spin-subatomic-particles-0. 6 pages.
"Spin (physics)," https://en.wikipedia.org/wiki/Spin_(physics). 11 pages.
Air Liquide. "Change Over Manifolds." https://industry.airliquide.US. 4 pages.
"Oxygen, Compressed," https://dailymed.nlm.nih.gov/dailymed/fda/fdaDrugXsl.cfm?setid=d41dee2b-8191-a5ec-6ca8-5b8edd7e3009&type=display. 14 pages.
Precision Medical, "Helium-Oxygen Blender Service Manual." 32 pages.
Wilcox, Anna, "Why Does Cannabis Work for so Health Conditions?" https://news.green-flower.com/why-does-cannabis-work-for-so-many-different-health-conditions/. Jul. 19, 2020. 9 pages.
Pertwee, R. G., "The diverse CB and CB receptor pharmacology of three plantcannabinoids: Δ-tetrahydrocannabinol, cannabidiol and Δ-tetrahydrocannabivarin." Br J Pharmacol. Jan. 2008; 153(2): 199-215. 34 pages.
Hashemian, et al. "The use of heliox in critical care." Int J Crit Illn Inj Sci. Apr.-Jun. 2014; 4(2): 138-142. 9 pages.
Reuben, A. D.; et al. "Heliox for asthma in the emergency department: a review of the literature." https://emj.bmj.com/content/21/2/131. 10 pages.
Lanz, Christian; et al. "Medicinal Cannabis: In Vitro Validation of Vaporizers for the Smoke-Free Inhalation of Cannabis." PLoS One. 2016; 11(1): e0147286. 21 pages.
Ruppel, Timothy D.; et al. "Cannabis Analysis: Potency Testing Identification and Quantification of THC and CBD by GC/FID and GC/MS." PerkinElmer, Inc. 6 pages.
Kaplan, Josh. "Is more CBD better? The science behind CBD dosing for anxiety and other conditions." www.leafly.com. 4 pages.
International search report dated Sep. 8, 2020, for related PCT application No. PCT/US2020/034419, filed on May 22, 2020.
Extended European Search Report for European Patent Application No. 20813756.2-1122, dated Dec. 7, 2022, 7 pages.

* cited by examiner

DUAL METERED INHALER

This application claims priority to provisional application Ser. No. 62/852,806 filed May 24, 2019, provisional application Ser. No. 62/966,389 filed Jan. 27, 2020, and provisional application Ser. No. 63/019,119 filed May 1, 2020, each of which is incorporated herein by reference.

FIELD OF THE INVENTION

The field of the invention is breathing inhalers.

BACKGROUND

The background description includes information that may be useful in understanding the present invention. It is not an admission that any of the information provided herein is prior art or relevant to the presently claimed invention, or that any publication specifically or implicitly referenced is prior art.

Many different types of nebulizers or other inhalers are known. One can characterize inhalers into two main types, (1) those that use pellets or other fixed dosage of physiologically active substance, and (2) those that have a reservoir of physiologically active substance, which is metered out in individual doses by the delivering mechanism. In either case there is usually a pressurized carrier gas that combines with the physiologically active substance to expel that substance into a mouthpiece, and then into the mouth and lungs of a user.

In some instances, (e.g., U.S. Pat. No. 6,125,844 to Samiotes et al.) it is also known to include a drug or other physiologically active substance in the pressurized gas, or even use helium, Oxygen or other gas that itself has a physiologic activity. In such instances it is important to meter the amount of pressurized gas delivered to the user. In known such devices, it appears that such metering cannot be set by the user.

In many instances, that limitation wouldn't matter, because the deliver device is sold for use with a particular drug. The wide usage of vaping has raised a need, however to provide a device that can be utilized with a range of different carrier gasses and physiologically active substances. The known devices are inadequate, where the user can only meter one of (a) the physiologically active substance and (b) the carrier gas, on a per dose basis.

U.S. Pat. No. 6,125,844 and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

SUMMARY OF THE INVENTION

The inventive subject matter provides apparatus, systems, and methods in which an inhaler comprises first and second user-operable controllers configured to independently meter first and second amounts of a physiologically active substance and a pressurized gas, respectively, to the user in the dose.

In preferred embodiments a regulator is configured to release a dose to the mouthpiece. Triggering can be activated by one or more of the user drawing a breath through the mouthpiece, and the user operating a trigger.

All suitable forms of physiologically active substances are contemplated, including liquids, solids, and gasses, and combination of these. In some embodiments a primary or additional physiologically active substance can be included in with the pressurized gas.

The pressurized gas can have any suitable pressure and contents. In some preferred embodiments the pressurized gas includes at least 10 wt % helium, and independently at least at least 30 wt % oxygen.

Any suitable controller can be used to meter the physiologically active substance(s) and the pressurized gas, including for example, physical knobs, sliders, and buttons. Digital controllers are also contemplated. Independent metering of the physiologically active substance(s) and the pressurized gas can be accomplished by setting fixed amounts for both, or setting a fixed amount for one (e.g., the physiologically active substance(s)), and then adjusting the other amount relative to the fixed amount.

Embodiments are contemplated in which the inhaler can communicate relevant data to an external device, for example using a hard-wired or wireless electronic communication circuit.

Embodiments are also contemplated in which the mouthpiece is either removable or not removable.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
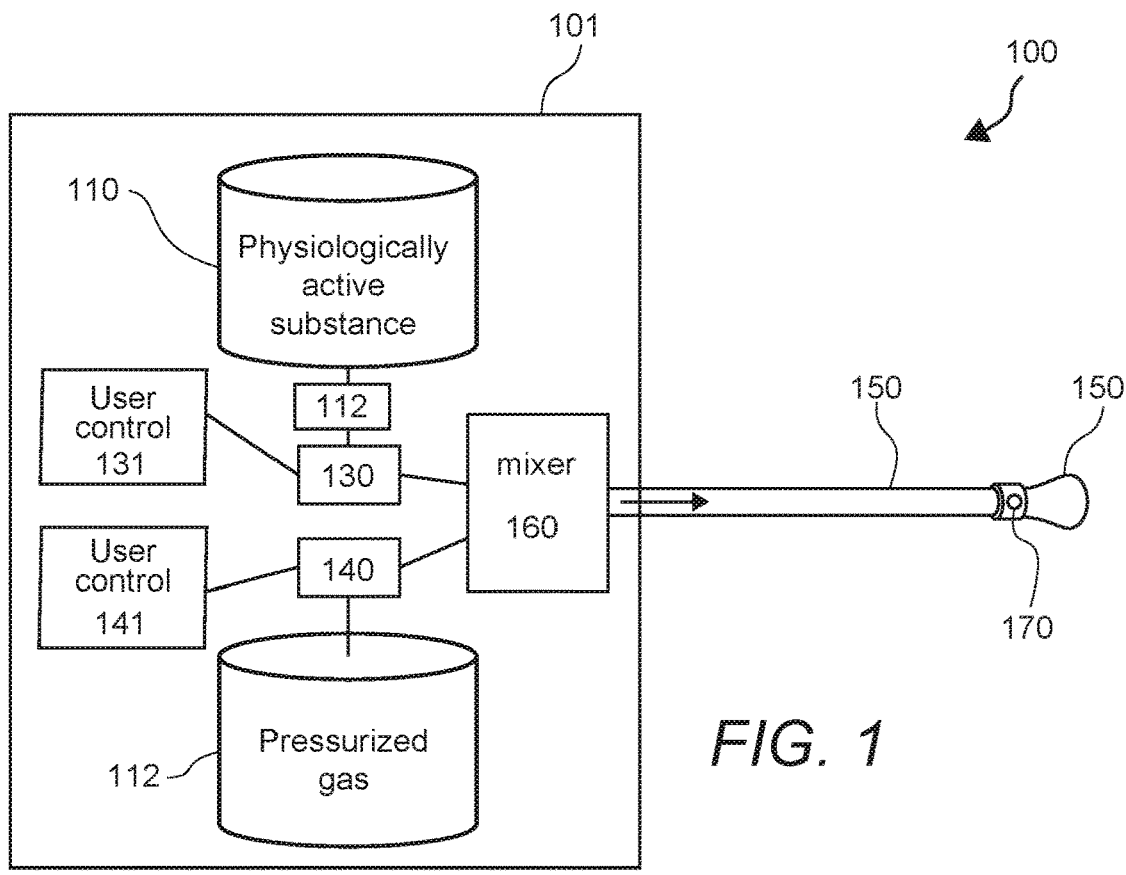
FIG. 1 is a generalized schematic of a contemplated inhaler.

One should appreciate that the disclosed subject matter provides many advantageous technical effects including providing inhalers with enhanced user control over amounts of inhaled physiologically active substance(s) and pressurized gas in discreet doses. Among other things, this allows a given inhaler to accommodate a wide range of different physiologically active substance(s) and pressurized gas/gasses, which can be particularly important when the pressurized gas/gasses includes helium.

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

In FIG. 1, an inhaler 100 generally includes a reservoir 110 that contains a user-replaceable physiologically active substance, a user-replaceable pressurized gas reservoir 120, a mixer 160, a tube 150 and a mouthpiece 180.

A processing unit 112 processes substance from reservoir 110, and passes processed substance along to regulator 130. Processing unit 112 0 can utilize an electrically powered an atomizer (not shown) to produce an aerosol containing individual amounts of the physiologically active substance. User control operates regulator 131. Regulator 140 regulates gas flowing from pressured gas reservoir 120 under control of user control 141. Processed physiologically active substance from regulator 130 and gas from regulator 140 is mixed in mixer 160 to produce a dose to be inhaled. A trigger button 170 either triggers release of the dose, or triggers potential release of the dose upon the user inhaling through the mouthpiece 180.

The amount of gas dispensed by regulator 140 can be adjusted in any suitable manner to provide a controlled flow rate, volume, and or pressure of the carrier gas that permits generation of an aerosol with an optimal volume, mean droplet size, droplet size dispersion, and/or droplet density (i.e. droplets/cc$^3$). Optimization can be directed to achieve a target dispersion (i.e. movement of material) and/or target deposition (i.e. region of the respiratory tract) for an FDA approved or holistic medicinal compound. In some embodiments the carrier gas can be applied directly into a portion of the device that is distal to the device's mouthpiece 410, with the stored carrier gas providing the entire gas content of the aerosol (i.e. the "closed loop" configuration). In other embodiments the flow valve can permit mixing of the carrier gas with ambient air (for example, providing about 5%, 10%, 15%, 20%, 25%, 30%, 35%, 40%, 45%, 50%, 55%, 60%, 65%, 70%, 75%, 80%, 85%, 90%, or more than about 90% ambient air in the final gas mixture). Embodiments in which the amount of ambient air mixed with the carrier gas is less than 50% can be referred to as "partially closed loop" systems. One advantage of being able to adjust the pressure of the released gas is that it can assist in filling the lungs, and delivering the medication for those patients with a pulmonary obstructive disease.

Any suitable gas can be used. Suitable low-density gases include helium, helium/nitrogen mixtures, helium/oxygen mixtures (such as heliox), and/or helium/air mixtures. The gas regulator 140 can optionally be used to mix atmospheric gas with gas obtained from the gas reservoir 120. It is contemplated that the pressurized gas can be at least 10 wt % helium, more preferably at least 20 wt % helium, still more preferably at least 40 wt % helium, and still more preferably at least 60 wt % helium. It is contemplated that the pressurized gas can be at least 30 wt % oxygen, more preferably at least 40 wt % oxygen, and still more preferably at least 60 wt % oxygen.

Either or both of regulators 130, 140 can have two or more positions or settings, which permit a flow valve to adjust any one or more of flow rate, pressure, or volume of the carrier gas dispensed during use. In some embodiments the flow valve can be a manually actuated valve that is placed in the proper position or configuration by the user. For example, such a manual valve can present as a rotary dial with two or more stops with markings that are indicative of the valve's flow characteristics when at a particular stop. In the case of gas regulator 140, such a flow valve could introduce only gas that is stored in the pressurized reservoir 120. In other embodiments the flow valve could provide a defined mixture of ambient air and stored carrier gas.

Either or both of regulators 130, 140 can include a motor, magnetically responsive fluid, or other flow control mechanism that can be actuated by an extrinsic control mechanism, for example, by application of electrical energy from a storage device (not shown).

The physiologically active substance contained in reservoir 110 can be present as a solid, liquid, gas, or any combination thereof. The physiologically active substance can be cannabinoid, CBD, or combination thereof. Inhaler 100 is also suitable for delivery of a wide range of pharmaceutically active FDA approved or holistic medicinal compounds. Such compounds can be selected to be active at the point of delivery (i.e. the respiratory tract) or systemically. Examples of locally active physiologically active substances include bronchial dilators, steroids, anti-inflammatory compounds, antibiotics, antivirals, and vaccines. Such locally active compounds can, of course, move to systemic circulation. It should be appreciated that each of such compounds can have different optima for deposition and/or dispersion.

In FIG. 1 the physiologically active substance reservoir 110 is physically separated from the gas reservoir 120. In other embodiments (not shown), the physiologically active substance and gas reservoirs can be physically combined into a single, user-replaceable cartridge.

Figure 2:
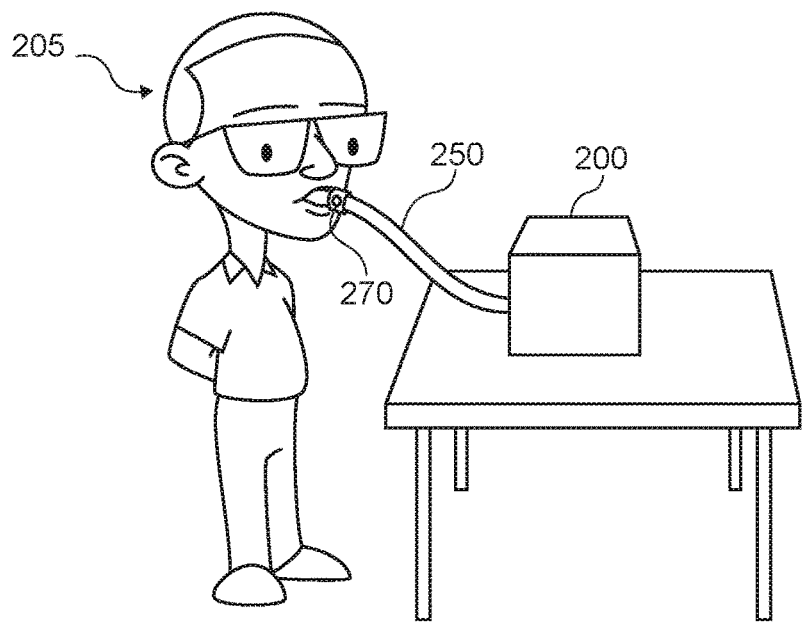
FIG. 2 is a schematic of a person using a desktop inhaler.

FIG. 2 shows a user 205 employing a inhaler in which a desktop component 200 passes doses through a tube 250 to a distal mouthpiece 270. The tube 250 can have any appropriate length, but would generally be less half a meter. Desktop embodiments are advantageous because where the various reservoirs, e.g., 110, 120, can be larger than in handheld units.

Figure 3:
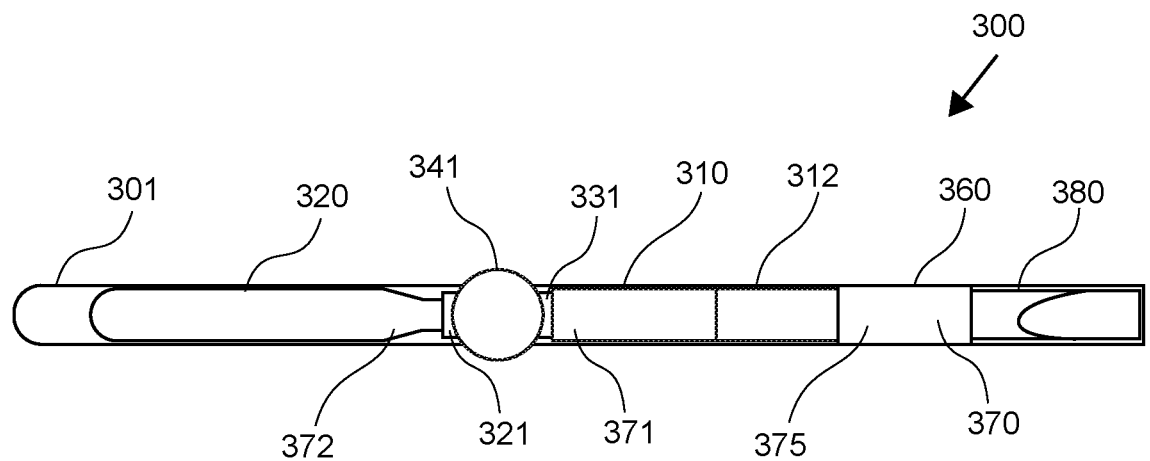
FIG. 3 is an open view of a contemplated inhaler, in which a cover has been removed to show a visible pressurized gas reservoir, a control knob for the pressurized gas, a visible reservoir for a physiologically active substance, and a digital control for that substance.

FIG. 3 shows a hand-held inhaler 300 that generally includes a housing 301 from which a cover has been removed to show a user-replaceable physiologically active substance reservoir 310, a user-replaceable pressurized gas reservoir 320, a mixer 360, and a mouthpiece 380.

A gas regulator 321 regulates gas flowing from pressured gas reservoir 320 under control of user control knob 341.

A processing unit 312 processes substance from reservoir 310, under control of digital controller 331. As described above, processing unit 312 can utilize an electrically powered an atomizer (not shown) to produce an aerosol containing individual amounts of the physiologically active substance.

Mixer 360 combines gas flowing from the gas regulator with the processed substance flowing from the processing unit 312.

In this embodiment, doses are released to the user by the user inhaling through the mouthpiece 380. A valve (not shown) controls such release. Trigger button 370 either directly triggers release of the dose, or triggers potential release of the dose upon the user inhaling through the mouthpiece 380.

The reservoirs 310 and 320 have machine-readable indicia 371, 372, respectively, which can be used by an electronic circuit 375 to provide relevant information to an external device (not shown). In such embodiments the controller 331 can be in communication with an information network (e.g. WiFi or cellular internet), which in turn can provide prescription and/or dosing information based on the user's medical history.

Figure 4:
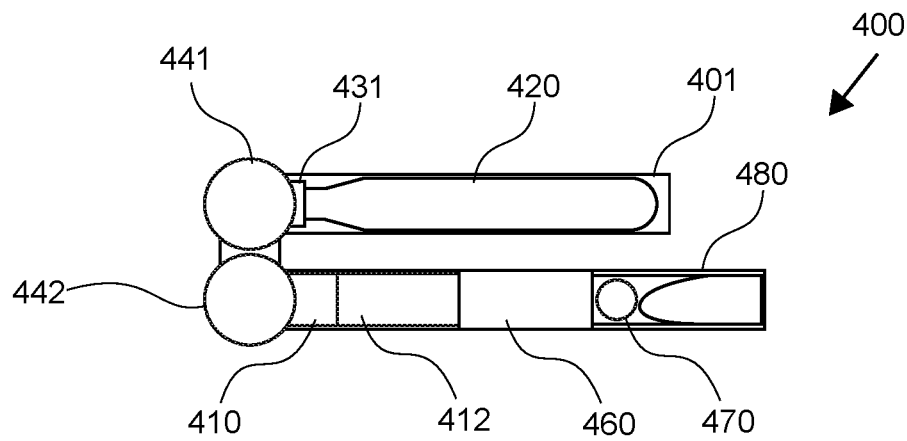
FIG. 4 is an open view of a different contemplated inhaler, in which a cover has been removed to show a pressurized gas reservoir, a control knob for the gas reservoir, a physiologically active substance reservoir, and a control knob for the physiologically active substance reservoir.

FIG. 4 shows a hand-held inhaler 400 that generally includes a housing 401 from which a cover has been removed to show a user-replaceable physiologically active substance reservoir 410, a user-replaceable pressurized gas reservoir 420, a mixer 460, and a mouthpiece 480.

A gas regulator 431 regulates gas flowing from pressured gas reservoir 420 under control of user control knob 441.

A processing unit 412 processes substance from reservoir 410, under control of user control knob 442. As described above, processing unit 412 can utilize an electrically powered an atomizer (not shown) to produce an aerosol containing individual amounts of the physiologically active substance.

Mixer 460 combines gas flowing from the gas regulator with the processed substance flowing from the processing unit 412.

In this embodiment, doses are released to the user by the user inhaling through the mouthpiece 480. A valve (not shown) controls such release.

Trigger button 470 either directly triggers release of the dose, or triggers potential release of the dose upon the user inhaling through the mouthpiece 480.

In any of the embodiments of FIGS. 1-4, an extrinsic control mechanism, (e.g. a smart phone or smart watch, not shown) could be used to direct operation of either or both of regulators (e.g., 131, 141).

Figure 5:
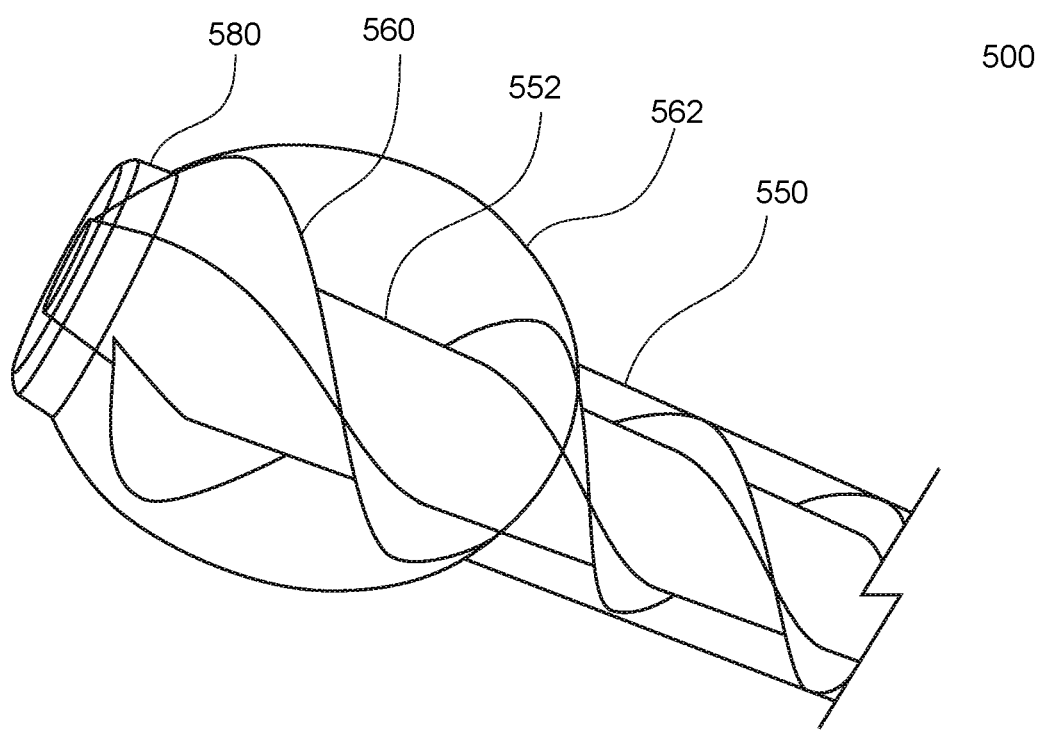
FIG. 5 is a perspective view of a conduction tube leading to a mouthpiece. The wall of the conduction tube is transparent to show a spiral conduction path.

In FIG. 5, an exit tube 500 is configured to cooperate with components 101 of the generalized inhaler of FIG. 1 or directly with regulators 130, 140 of components 101. Exit tube 500 generally includes an outer tube 550 leading to a mouthpiece 580. Within the outer tube 550 is an inner tube 552, about which is disposed a spiral pathway 560 and a bulb 562. It is contemplated that heliox or other gas from a pressurized gas reservoir travels along the spiral pathway 560 between the inner and outer tubes 552, 550, and processed physiologically active substance travels within the inner tube 552 as an aerosol.

It should be apparent to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. An inhaler that utilizes a mouthpiece to deliver a dose to a user, of (a) a physiologically active substance and (b) a pressurized gas, the inhaler comprising:
   at least first and second user-operable controllers configured to independently meter first and second amounts of the physiologically active substance and the pressurized gas, respectively;
   an exit tube having an inner tube within an outer tube and a fin between the inner and outer tubes;
   wherein the fin defines a first pathway between the outer and inner tubes configured to receive the pressurized gas; and
   wherein the inner tube comprises a second pathway configured to receive the physiologically active substance.

2. The inhaler of claim 1, further comprising a regulator configured to release the dose to the mouthpiece, triggered at least in part (1) by the user drawing in a breath through the mouthpiece or (2) by the user operating a trigger.

3. The inhaler of claim 1, wherein the exit tube is disposed within the mouthpiece.

4. The inhaler of claim 3, wherein the first pathway is spiraled.

5. The inhaler of claim 1, further comprising a regulator configured to release the dose to the mouthpiece, triggered by a combination of (a) the user operating a trigger and (b) the user concurrently drawing in a breath through the mouthpiece.

6. The inhaler of claim 1, wherein the physiologically active substance is stored in a reservoir as a liquid or a solid.

7. The inhaler of claim 1, wherein at least one of the physiologically active substance and the pressurized gas is stored in a user-replaceable reservoir.

8. The inhaler of claim 1, wherein the pressurized gas includes at least 10 wt % helium.

9. The inhaler of claim 1, wherein the pressurized gas includes at least 10 wt % helium, and at least 30 wt % oxygen.

10. The inhaler of claim 1, wherein the pressurized gas includes at least 10 wt % helium and at least 60 wt % oxygen.

11. The inhaler of claim 1, wherein at least one of the user-operable controllers is a physical knob.

12. The inhaler of claim 1, wherein at least one of the user-operable controllers comprises a digital control.

13. The inhaler of claim 1, wherein the first user-operable controller is configured to set the amount of the physiologically active substance to be delivered in the dose.

14. The inhaler of claim 1, wherein the second user-operable controller is configured to set the amount of the pressurized gas to be delivered in the dose.

15. The inhaler of claim 1, wherein the second user-operable controller is configured to set the amount of the pressurized gas relative to the amount of the physiologically active substance to be delivered in the dose.

16. The inhaler of claim 1, further comprising an electronic communication circuit configured to deliver data from the inhaler to an external device.

17. The inhaler of claim 1, further comprising a mouthpiece fitting configured to allow a user to replace the mouthpiece.

18. A method of providing a drug to a person, comprising:
providing an inhaler that utilizes a regulator to release to the person (a) a first amount of a physiologically active substance and (b) a second amount of a pressurized gas upon suction by the person upon a mouthpiece of the inhaler, wherein one or more of (1) the first amount of the physiologically active substance and (2) the second amount of the pressurized gas travels through (a) a pathway within an inner tube and (b) a pathway between an outer tube and the inner tube having a fin, when the dose is released to the mouthpiece.

19. The method of claim 18, further comprising the person adjusting at least one of (a) the first amount released to the person, (b) the second amount released to the person, and a relative mixture of the first and second amounts released to the person.

20. The method of claim 18, further comprising utilizing helium or Heliox in the pressurized gas.

* * * * *